United States Patent [19]

Lau et al.

[11] Patent Number: 4,695,655

[45] Date of Patent: Sep. 22, 1987

[54] ETHYNYLTHIOPHENOXY DERIVATIVES OF DIPHENYLHEXAFLUOROPROPANE

[75] Inventors: Kreisler S. Y. Lau, Alhambra; William J. Kelleghan, Whittier, both of Calif.

[73] Assignee: Hughes Aircraft Company, Los Angeles, Calif.

[21] Appl. No.: 647,000

[22] Filed: Sep. 4, 1984

[51] Int. Cl.[4] .............................................. C07C 149/34
[52] U.S. Cl. ...................................... 568/56; 524/371; 526/285; 568/637
[58] Field of Search ....................... 568/53, 56, 637, 57

[56] References Cited

U.S. PATENT DOCUMENTS 3,450,772  6/1969  Bridger et al. ...................... 568/316
4,374,291  2/1983  Lau ....................................... 568/58

FOREIGN PATENT DOCUMENTS 2102591  4/1972  France ................................. 568/636

OTHER PUBLICATIONS

R. Bridger et al., Chem. Abstracts 72: 12363v (1970) Poly (Phenyl Ethers).
J. Fried et al., Chem. Abstracts 100:86542w (1984), Mechanical Properties of Bisphenol-A Polysulfone and Acetylene Terminated Bisphenol-A Blends.
G. Loughran et al., Chem. Abstracts 97:39697k (1982). Thermal and thermomechanical properties of acetylene terminated.

*Primary Examiner*—Donald G. Daus
*Assistant Examiner*—Mary E. Ceperley
*Attorney, Agent, or Firm*—M. E. Lachman; A. W. Karambelas

[57] ABSTRACT

Ethynylphenyl derivatives of diphenylhexafluoropropane having the formula:

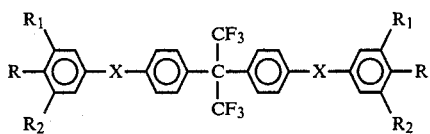

where X is oxygen or sulfur and each of R, $R_1$, or $R_2$ is hydrogen or ethynyl. The compounds are useful in forming polymer structures, either homopolymers or copolymers.

2 Claims, 2 Drawing Figures

ETHYNYLTHIOPHENOXY DERIVATIVES OF DIPHENYLHEXAFLUOROPROPANE

BACKGROUND OF THE INVENTION

1. Field of the Invention

The present invention relates generally to diethynylated aromatic compounds. More particularly, the present invention relates to diphenylhexafluoropropane compounds having an ethynylphenoxy or ethynylthiophenoxy group attached to the phenyl rings of the diphenylhexafluoropropane.

2. Description of the Background Art

Diethynylated aromatic compounds are important intermediates in the synthesis of thermally stable resins for use in high-temperature structural composites, and high-char yielding structure matrices, such as carbon-carbon composites. These materials are used in the fabrication of reentry missile nose cones, leading edges, rocket nozzles, and other structural applications requiring high structural strength and high thermal stability.

The processing and fabrication of these high temperature resins is generally rather difficult. When using the diethynylated aromatic compounds by themselves or as diluents in various high temperature resins and composite products, it is important that the compound be in a fluid state over a relatively large workable temperature range in order to facilitate processing. This workable or fluid temperature range is generally referred to as the "processing window" for the given diethynylated aromatic compound. The lower limit of the processing window is the temperature at which the compound melts to a liquid state, while the upper limit is the temperature at which the compound gels and solidifies. If possible, it is desirable to use compounds which have processing windows encompassing ambient temperatures in order to simplify resin fabrication and make the process commercially practical.

There are presently only two known diethynylated aromatic compounds which are viscous liquids at ambient temperatures. One is an acetylene-terminated sulfone (ATS) and the other is 2,2-bis(4-ethynylphenyl) hexafluoropropane (EPHFP). EPHFP and related compounds are disclosed in U.S. Pat. No. 4,374,291 which issued Feb. 15, 1983, to the same assignee as the present invention. It would be desirable to provide additional diethynylated aromatic compounds which have processing windows in the same range as the above discussed known compounds and which also provide additional properties and characteristics not found in either of the two known compounds.

SUMMARY OF THE INVENTION

In accordance with the present invention, new diethynylated aromatic compounds are disclosed which have a large processing window which extends from 71° C. to 225° C. The new compounds cure to yield cross-linked networks that are more highly thermally stable than the known ATS or EPHFP compounds and which have higher glass transition temperatures.

The compounds in accordance with the present invention are ethynylphenoxy and ethynylthiophenoxy derivatives of diphenylhexafluoropropane which have the following formula:

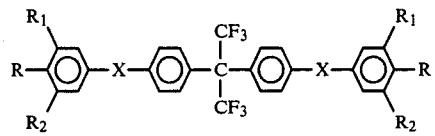

where X is oxygen or sulfur and each of R, $R_1$, or $R_2$ is hydrogen or ethynyl. In the preferred compositions, $R_1$ and $R_2$ are hydrogen and R is ethynyl.

The large processing window of the new compounds allows easy handling and blending with other high temperature oligomers and polymers, thus acting as a compatible diluent to improve processing of the high temperature polymer materials which are otherwise difficult to process. (The term compatibility is generally referred to herein to mean the avoidance of phase separation of the blended polymers in the resin mixture.) In addition, blending and copolymerization of the new compounds with other acetylene-terminated oligomers yields interpenetrating copolymer networks that are suitable structural materials for high temperature applications.

The compounds of the present invention are also useful as plasticizing diluents for use in processing high molecular weight thermoplastics. Curing of high molecular weight thermoplastics with the compounds of the present invention incorporated therein produces a cross-linked network within the thermoplastic to enhance the high temperature structural strength of the thermoplastic.

As another feature of the present invention, the presence of flexible oxygen or sulfur linkages (X) between the hexafluoroisopropylidene groups and the ethynylphenyl groups, along with the large molecular distance between the ethynyl end groups yields polymers and copolymers having improved resistance to fracturing.

The above-discussed and many other features and attendant advantages of the present invention will become apparent as the invention becomes better understood by reference to the following detailed description when considered in conjunction with the accompanying drawings.

DETAILED DESCRIPTION OF THE INVENTION

Compounds in accordance with the present invention have the general formula:

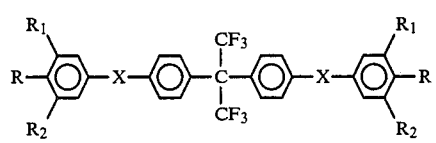

where X is oxygen or sulfur and each of R, $R_1$ or $R_2$ is hydrogen or ethynyl. A preferred compound is 2,2- bis[4-(4-ethynylphenoxy)phenyl]hexafluoropropane where X is oxygen, $R_1$ and $R_2$ are hydrogen and R is ethynyl. Another preferred compound is 2,2-bis[4-(4-ethynylphenylthio)phenyl]hexafluoropropane where X is sulfur, $R_1$ and $R_2$ are hydrogen and R is ethynyl. Exemplary preparation of these two preferred embodiments are as follows.

Figure 1:
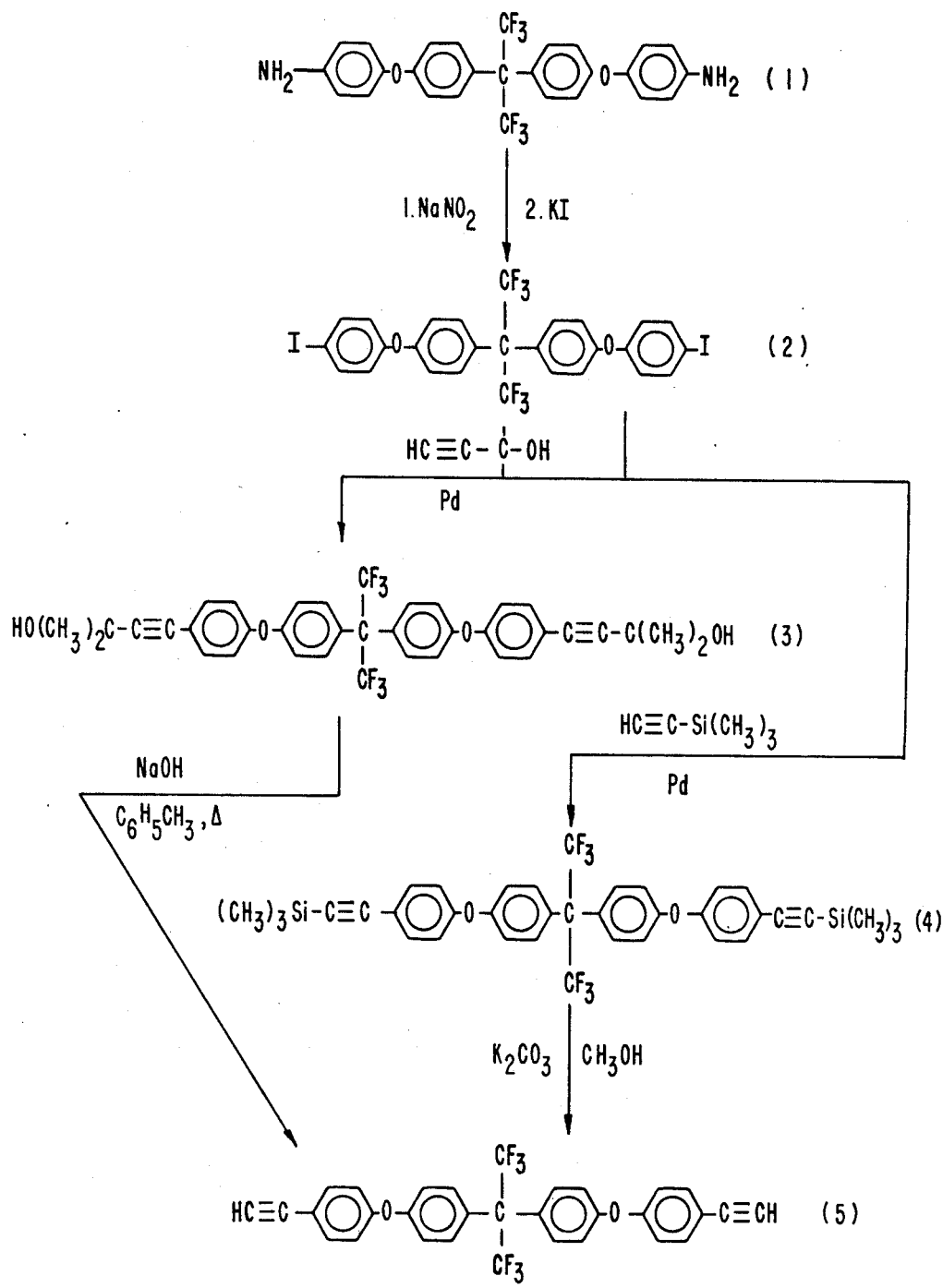
FIG. 1 is a schematic representation of two alternate exemplary processes for preparing a preferred ethynylphenoxy derivative of diphenylhexafluoropropane in accordance with the present invention.

The preparation of 2,2-bis[4-(4-ethynylphenoxy)-phenyl]hexafluoropropane (5) is shown schematically in FIG. 1. The 2,2-bis[4-(4-ethynylphenoxy)phenyl]hexa-fluoropropane (5) can be made by two preferred synthesis routes. Each route involves preparation of 2,2-bis[4-(4-iodophenoxy)phenyl]hexafluoropropane (2) followed by reaction with either 2-methyl-3-butyn-2-ol or ethynyltrimethysilane to produce the intermediates (3) and (4) respectively as shown in FIG. 1. Each of the two intermediates is then treated as discussed below to form the desired 2,2-bis[4-(4-ethynylphenoxy)phenyl]-hexa-fluoropropane (5).

Examples of practice are as follows.

EXAMPLE 1

This example illustrates the preparation of 2,2-bis[4-(4-ethynylphenoxy)phenyl]hexafluoropropane (5) in accordance with the present invention.

A. Preparation of 2,2-Bis[4-(4-iodophenoxy)phenyl]hexafluoropropane (Compound 2)

2,2-Bis[4-(4-iodophenoxy)phenyl]hexafluoropropane (Compound 2) was prepared by first placing 250 ml of concentrated hydrochloric acid in a 4-liter beaker. While being stirred mechanically, the acid was treated with 103.6 grams (0.2 mole) of 2,2-bis[4-(4-aminophenoxy)-phenyl]hexafluoropropane (1) (available from Morto Chemical Company as 4-BDAF). To this slurry was added 400 grams of ice to give a final temperature of $-15°$ C. By drop-by-drop addition, a 500 ml aqueous solution of 30.4 grams (0.44 mole) of sodium nitrite was added. As heat was generated, the reaction mixture must be controlled at a temperature range of $-5°$ C. to $0°$ C. by the addition of ice. At the end, the slurry changed to a reddish brown solution which turned KI starch paper blue. The solution was stirred for an additional 0.5 hr at 0° C. A solution of 73 grams (0.44 mole) of potassium iodide in 250 ml of water was added at such a rate that foaming was under control. After the addition of potassium iodide, the mixture was allowed to stand at 25° C. for 16 hrs.

The solution was neutralized and extracted in several portions with a total of 2 liters of dichloromethane. The organic phase was washed with $3\times500$ ml of aqueous sodium bisulfite, $1\times500$ ml of aqueous sodium bicarbonate and $2\times500$ ml of water. After drying over magnesium sulfate and concentrating, 121.9 grams of a brown solid was obtained and was purified by silica gel column chromatography using 1:10 dichloromethane-hexane as eluant. At the end, 70.4 grams of a creamy-white solid was obtained: M.P. 128°–131° C.

A second silica gel column chromatography on a 1 gram sample of the product noted immediately above afforded lustrous white rhombic crystals of 2,2-bis[4-(4-iodophenoxy)phenyl]hexafluoropropane (2) which was melted at 140°–141° C.

The physical properties for the compound (2) are:
IR (KBr): 3170 (weak), 1620, 1585, 1515, 1485, and very strong absorption at 1300–1175 cm$^{-1}$;

NMR (CDCl$_3$): δ6.74–7.80 ppm (2 overlapping distorted AB splitting patterns.)

B. Preparation of 2,2-Bis[4-[4-(3-hydroxy-3-methylbut-1-ynyl)phenoxy]-phenyl]hexafluoropropane (Compound 3)

To a solution of 59.2 grams (0.08 mole) of Compound 2 in 300 ml of deaerated anhydrous triethylamine (Fluka), were added 250 mg of (Ph$_3$P)$_2$PdCl$_2$, as the precursor for zero valent palladium. The mixture was heated at approximately 45° C. with stirring until all particles had dissolved. As one portion, 14.8 g (0.176 mole) of 2-methyl-3-butyn-2-ol was added followed by 68.5 mg of Cu$_2$I$_2$. The temperature of the oil bath was raised to about 95°–100° C. and maintained in this range for 4.5 hrs. After cooling and diluting with 300 ml of ether, the slurry was filtered to yield 34.07 g of triethylamine hydroiodide (0.149 mole, 93% of theory).

The filtrate was concentrated to dryness, redissolved in 200 ml of dichloromethane and washed with 100 ml each of 10% hydrochloric acid, water, saturated sodium bicarbonate and water again. After drying over magnesium sulfate and concentrating, the residue was purified by silica gel column chromatography. Elution with hexane removed the diacetylene side product. Eluting with acetone and concentrating the eluate yielded a tan solid (51.9 g, 0.080 mole, 99.5% of theory) which was identified as Compound 3. Compound 3 had the following properties: M.P. 73°–77° C.; IR (film): 3400 (broad, strong OH), 3000 (sharp, strong methyl), 2240 (weak, C—C), 1600, 1505, and 1300–1140 cm$^{-1}$ (strong, broad); NMR (acetone-d$_6$): δ1.05 (s,12 H,CH$_3$), 6.40–7.05 ppm (2 overlapping A$_2$B$_2$ quartets, 16 H, aromatic H's).

Analysis for C$_{37}$H$_{30}$F$_6$O$_4$ (444.407):
Calculated: C, 68.09; H, 4.63.
Found: C, 68.17; H, 4.89.

C. Preparation of 2,2-Bis[4-(4-ethynylphenoxy)phenyl]hexafluoropropane (Compound 5) from 2,2-[4-[4-(3-Hydroxy-3-methylbut-1-ynyl)phenoxy]-phenyl]hexafluoropropane (Compound 3)

A solution of 0.32 grams (0.008 mole) of sodium hydroxide in 5 ml of water was added to 31.9 grams (0.050 mole) of Compound 3 in 150 ml of toluene. After refluxing for 2 hours, the mixture was then azeotropically distilled. The cloudy liquid that distilled contained acetone.

After cooling, the mixture was washed with 100 ml of water, dried over magnesium sulfate, and concentrated to a solid mass. The solid mass was purified by column chromatography eluting with hexane. The pale yellow solid was identified as 2,2-bis[4-(4-ethynylphenoxy)-phenyl]hexafluoropropane (Compound 5) by the characteristic 2210 cm$^{-1}$ absorption in its IR spectrum and also by the distinctive singlet at δ3.14 ppm and a distorted AB pattern at δ6.90–7.85 ppm in its NMR spectrum.

D. Preparation of 2,2-Bis[4-(4-trimethylsilylethynylphenoxy)phenyl]hexa-fluoropropane (Compound 4)

To a solution of 26.45 grams (35.74 mmoles) of Compound 2, prepared as noted above, in 200 ml of deaerated, anhydrous triethylamine, was added the catalyst system which comprised 48 mg of palladium[II]acetate and 200 mg of triphenylphosphine, and which provides, upon reduction, zero valent palladium. The cloudy yellow solution was stirred and heated at 50° C. until all of the brown particles dissolved. Ethynyltrimethylsilane (8.760 g, 89.39 mmoles) was added and the mixture was rapidly heated to 70° C. over 5 minutes. At 60° C., a clear yellow solution was obtained. At 70° C., precipitation of the white triethylamine hydroiodide commenced. The reaction temperature was raised to 90°-95° C. over 10 minutes and maintained at that temperature range for 6 hours. After one hour, an unexpected decomposition of the palladium complex took place and the white precipitate took on a grey color. The slurry was then cooled, diluted with 100 ml of ether and filtered. The grey solid was washed with more ether and air-dried. A virtually quantitative yield (15.64 g, 71.42 mmoles) of triethylamine hydroiodide was realized.

The dark brown filtrate was concentrated, dissolved in 200 ml of ether and washed with 100 ml each of 10% hydrochloric acid, water, saturated sodium bicarbonate adn water again. The ethereal phase was dried over magnesium sulfate and concentrated to a foamy semi-solid. The crude yield was virtually quantitative. A one-gram sample was removed and was purified by column chromatography. The second band travelled down the column was eluted with 1.5 liters of hexane. The eluate was concentrated to a molasses consistency to provide a light yellow semi-solid 2,2-bis[4-(4-trimethylsilylethynylphenoxy)phenyl]hexafluoropropane (Compound 4).

E. Alternative Preparation of 2,2-Bis[4-(4-ethynylphenoxy)phenyl]hexafluoropropane (Compound 5) from 2,2-Bis-[4-(4-trimethylsilylethynylphenoxy)-phenyl]hexafluoropropane (Compound 4)

The light yellow semi-solid (Compound 4) obtained immediately above was dissolved in 200 ml of a mixture of 1:1 anhydrous methanol-tetrahydrofuran and stirred with 2 grams of anhydrous potassium carbonate at 25° C. for 16 hours. The solution turned dark orange brown after one hour. Removal of the solvent left a solid residue which was dissolved in 200 ml of ether and washed with 2×200 ml of water. The ethereal fraction was dried over magnesium sulfate and concentrated to a viscous oil. Silica gel column chromatography eluting with 9:1 hexane-dichloromethane gave a white low melting solid which was identified as 2,2-bis[4-(4-ethynylphenoxy)phenyl]hexafluoropropane (Compound 5). The IR and NMR spectra were as follows:

IR (KBr): 3310 (strong, C≡C—H), 2200 (weak, C≡C).

NMR (CDCl$_3$) δ3.14 (s, 2H, C≡C—H) and 6.90-7.85 ppm (distorted AB quartet, 16 H, aromatic).

EXAMPLE 2

This example illustrates the preparation of 2,2-bis-[4-(4-ethynylphenylthio)phenyl]hexafluoropropane in accordance with the present invention.

Figure 2:
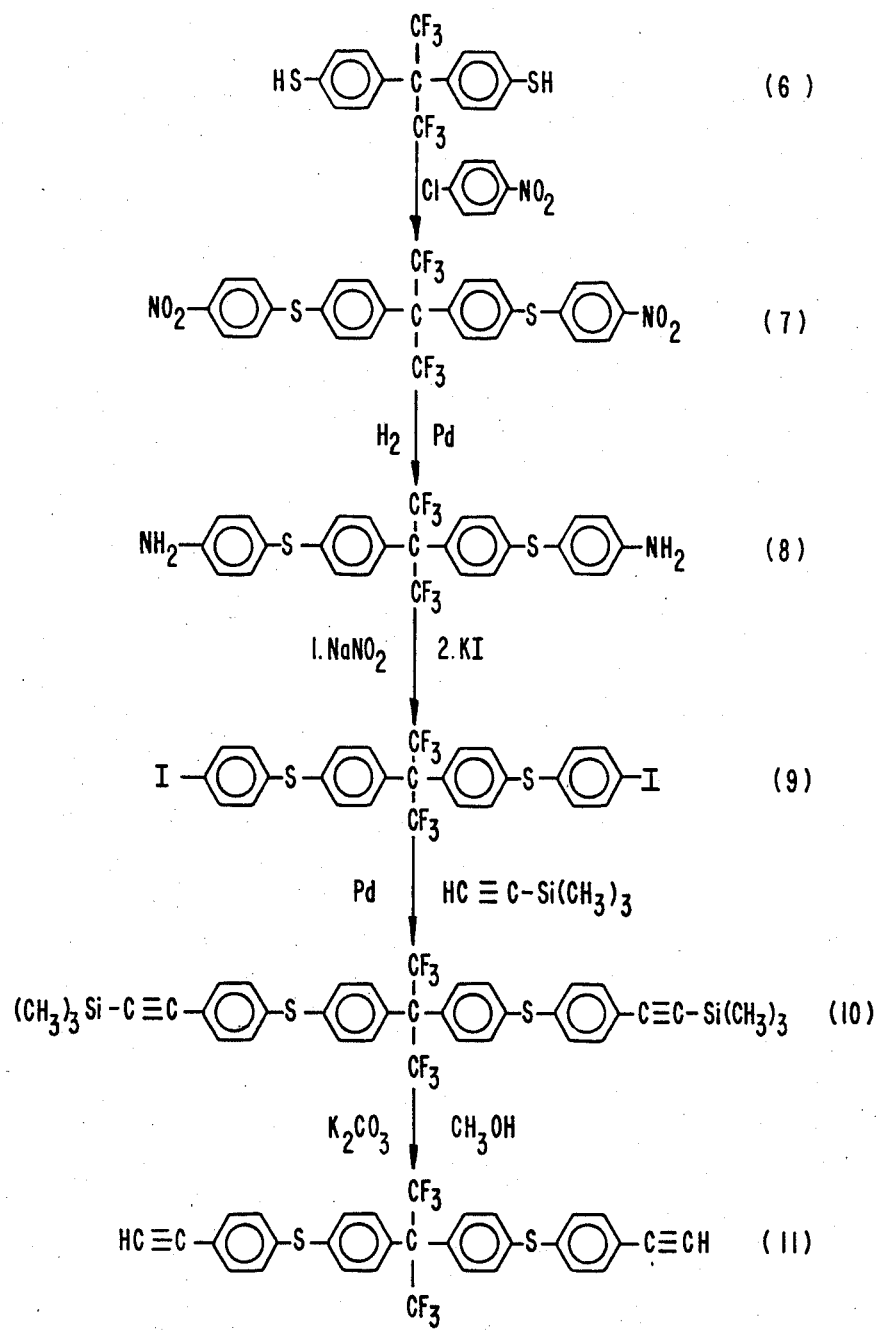
FIG. 2 is a schematic representation of an exemplary process for preparing a preferred ethynylthiophenoxy derivative of diphenylhexafluoropropane in accordance with the present invention.

The preparation of 2,2-bis[4-(4-ethynylphenylthio)-phenyl]hexafluoropropane (11) is shown schematically in FIG. 2. An exemplary synthesis in accordance with the procedure set forth in FIG. 2 is as follows.

A. Preparation of 2,2-Bis(4-mercaptophenyl)hexafluoropropane (Compound 6)

Compound 6 and related bis(benzenethiol) compounds are disclosed in co-pending patent application Ser. No. 453,431, filed Dec. 27, 1982 and assigned to the same assignee as the present invention. Compound 6 and the related compounds are prepared in a three-step process. In the first step, a bisphenol is reacted with N,N-dimethylthiocarbamoyl chloride in the presence of a base. Preferably, a 10% to 20% molar excess of the carbamoyl chloride to bisphenol is used in this reaction. The preferred temperature for the reaction is in the range of about 0° C. to about 60° C. at atmospheric pressure. The preferred time of reaction is in the range of about one to about two hours. From this first step of the process, a class of compounds called O-thiocarbamate esters is obtained.

In the second step of the process, the O-thiocarbamate esters from the first step are heated at a temperature in the range of about 150° C. to about 275° C. for a period in the range of about one to about two hours and at atmospheric pressure, preferably under an inert atmosphere such as argon, to form a class of compounds called S-thiocarbamate esters. The rearrangement reaction is known by the general term "Smiles Rearrangement".

In the third step of the process, the S-thiocarbamate esters from the second step are treated with a strong base such as potassium hydroxide in methanol, and then treated with a concentrated acid such as hydrochloric or nitric to form the desired bis(benzenethiol).

The following example illustrates the formation of the bis(benzenethiol) (Compound 6).

To a solution of 112 grams (0.33 mole) of Bisphenol AF [2,2-bis(4-hydroxyphenyl)hexafluoropropane] in 700 milliliters of benzene was added 43.5 grams (0.66 mole) of 85% potassium hydroxide. The resulting solution was refluxed with a trap to remove water; benzene was then removed at reduced pressure. To the resulting salt was added 700 milliliters of dimethylformamide, the mixture was then cooled to 0° C., and then 100 grams (0.81 mole) of N,N-dimethylthiocarbamyl chloride was added. The resulting mixture was heated to room temperature, then to 60° C., and maintained at 60° C. for one hour.

The product mixture was diluted with three liters of water and extracted twice with an 80:20 benzene/hexane solution. The organic phase was evaporated under reduced pressure to obtain a solid crystalline residue. The residue was recrystallized from a 5:1 methanol/benezene solution to obtain 125 grams of a product melting at about 209°-211° C. This product was the O-thiocarbamate ester of Bisphenol AF.

Fifteen grams (0.3 mole) of the O-thiocarbamate ester of bisphenol AF was placed in a reaction vessel, and heated at 250° C. under argon for one hour. After cooling the product to room temperature, the glassy residue was recrystallized from 60 milliliters of methanol to obtain 11 grams of a product having a melting point of 141°-144° C. This product was the S-thiocarbamate ester of the bisbenzenethiol derivative.

Seventy-five grams (0.15 mole) of the above S-thiocarbamate ester was then placed in 400 milliliters of methanol, and a solution of 75 grams of potassium hydroxide in 200 milliliters of water was added. This mixture was refluxed for one hour, cooled and diluted with two liters of water. A solution of 165 milliliters of concentrated HCl in one liter of water was then added. A precipitate was obtained which was recrystallized from a 3:1 methanol-water mixture to obtain 50 grams of the product 2,2-bis(4-mercaptophenyl)hexafluoropropane (Compound 6). The dipotassium salt of Compound 6 was formed by reacting Compound 6 with a potassium-containing base.

B. Preparation of 2,2-Bis[4-(4-nitrophenylthio)phenyl]hexafluoropropane (Compound 7)

Compound 7 was synthesized by a nucleophilic aromatic substitution reaction between the dipotassium salt of Compound 6 and 2 equivalents of 4-chloronitrobenzene in dimethyl sulfoxide at 150°–160° C.

C. Preparation of 2,2-Bis[4-(4-aminophenylthio)phenyl]hexafluoropropane (Compound 8)

Compound 8 was is prepared by hydrogenating 2,2-bis[4-(4-nitrophenylthio)phenyl]hexafluoropropane (Compound 7) in a Parr apparatus under 4 atmospheres of hydrogen over palladium-on-charcoal catalyst in ethyl alcohol solvent.

D. Preparation of 2,2-Bis[4-(4-iodophenylthio)phenyl]hexafluoropropane (Compound 9)

Compound 9 was prepared by treating Compound 8 with sodium nitrite followed by potassium iodide according to the general diazotization procedure described in Example 1, Section A herein.

E Preparation of 2,2-Bis[4-(4-trimethylsilylethynylphenylthio)phenyl]-hexafluoropropane (Compound 10)

Compound 10 was prepared by treating Compound 9 with the palladium catalyst system and ethynyltrimethylsilane according to the general procedure described in Example 1, Section D herein.

F. Preparation of 2,2-Bis[4-(4-ethynylphenylthio)phenyl]hexafluoropropane (Compound 11)

The final desired product 2,2-bis[4-(4-ethynylphenylthio)phenyl]hexafluoropropane (Compound 11) was prepared by treating Compound 10 with anhydrous methanoltetrahydrofuran and anhydrous potassium carbonate according to the general procedure described in Example 1, Section E herein.

Compounds in accordance with the present invention may be utilized to form homopolymers or they may be copolymerized with various other ethynylated monomers such as acetylene-terminated sulfones (ATS) and acetyleneterminated imides. The amount of ethynylated monomers incorporated into the copolymer may be varied depending upon desired properties for the copolymer. Copolymers with from 1 to 99 weight percent ethynylated monomers are possible.

In addition, the compounds may be used as plasticizing diluents in the preparation of various high temperature resins such as polyimides, polybenzothiazoles, polyquinolines, and polyquinoxalines. When used as a plasticizing diluent, the compounds are preferably added to the resins in amounts ranging from a few weight percent up to about 30 weight percent. The amount of the present compounds added as a plasticizer can be varied to achieve desired improvements during handling and processing of the resin along with desired reductions in brittleness of the final resin product.

EXAMPLE 3

A homopolymer of 2,2-bis[4-(4-ethynylphenoxy)phenyl]hexafluoropropane was prepared by heating a sample of the neat material from 52° C. to 315° C. in a button mold at the rate of 2°–3° C. per minute. The resulting button was cured at 316° C. for 2 hours. The cured button had a glass transition temperature of approximately 333° C. The polymer was stable, i.e. exhibited no weight loss during thermogravimetric analysis up to temperatures of above 500° C. The cured button was also post-cured for a total of 24 hours at a temperature of 316° C. The resulting post-cured button had a glass transition temperature of about 370° C.

EXAMPLE 4

A copolymer of 1 part of 2,2-bis[4-(4-ethynylphenoxy)phenyl]hexafluoropropane and 4 parts of an acetylene-terminated polyimide oligomer of the type described in U.S. Pat. No. 4,438,273 at columns 9–10 with an average degree of polymerization (DP) of 15 was prepared by heating a sample of the mixture in a button mold from 52° C. to 315° C. at the rate 2° C. per minute. The resulting button was cured at 316° C. for 24 hrs. The cured button had a glass transition temperature of approximately 325° C., and thermogravimetric analysis showed no weight loss up to 500° C.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A diphenylhexafluoropropane compound having the formula:

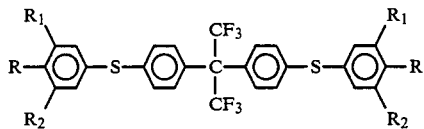

where R, $R_1$ and $R_2$ are hydrogen or ethynyl.

2. A diphenylhexafluoropropane compound according to claim 1 where R is ethynyl and $R_1$ and $R_2$ are hydrogen.

* * * * *